United States Patent [19]
Chrzan et al.

[11] Patent Number: 5,723,036
[45] Date of Patent: Mar. 3, 1998

[54] ELECTROCHEMICAL MEASURING CELL

[75] Inventors: Rigobert Chrzan, Bad Oldesloe; Christoph Bernstein, Lübeck, both of Germany

[73] Assignee: Drägerwerk Aktiengesellschaft, Lübeck, Germany

[21] Appl. No.: 713,474

[22] Filed: Sep. 13, 1996

[30] Foreign Application Priority Data

Sep. 13, 1995 [DE] Germany ............... 19533911.8

[51] Int. Cl.⁶ .................................................. G01N 27/404
[52] U.S. Cl. .................. 204/415; 204/412; 205/782.5; 205/783
[58] Field of Search .................... 204/412, 415; 205/775, 782, 782.5, 783

[56] References Cited

U.S. PATENT DOCUMENTS

| | | | |
|---|---|---|---|
| 3,855,096 | 12/1974 | Bergman | 204/415 |
| 4,172,770 | 10/1979 | Semersky et al. | 204/415 |
| 4,377,446 | 3/1983 | Albery | 204/415 |
| 5,298,146 | 3/1994 | Braden et al. | 204/415 |

FOREIGN PATENT DOCUMENTS

| | | |
|---|---|---|
| 0126623 | 11/1984 | European Pat. Off. . |
| 4136779 | 5/1993 | Germany . |

*Primary Examiner*—T. Tung
*Attorney, Agent, or Firm*—Walter Ottesen

[57] ABSTRACT

The invention is directed to an electrochemical measuring cell 1 for detecting different gas components. The electrochemical measuring cell includes several measuring electrodes (8, 12, 13), a common counter electrode 21 and a common reference electrode 20 in an aqueous electrolyte 3. The measuring electrodes each include a diffusion membrane (7, 11) and individual diaphragms (9, 14) limiting the inflow of gas to the individual measuring electrodes (8, 12). The diffusion membranes (7, 11) cover the measuring electrodes (8, 12, 13). The measuring cell 1 is so improved that the selectivity of the detection of different gas components is improved. An electrolyte barrier 19 is provided at least between one of the measuring electrodes 8 and the remaining measuring electrodes (12, 13). The electrolyte barrier 19 prevents lateral diffusion within the diffusion membrane (7, 11).

3 Claims, 1 Drawing Sheet

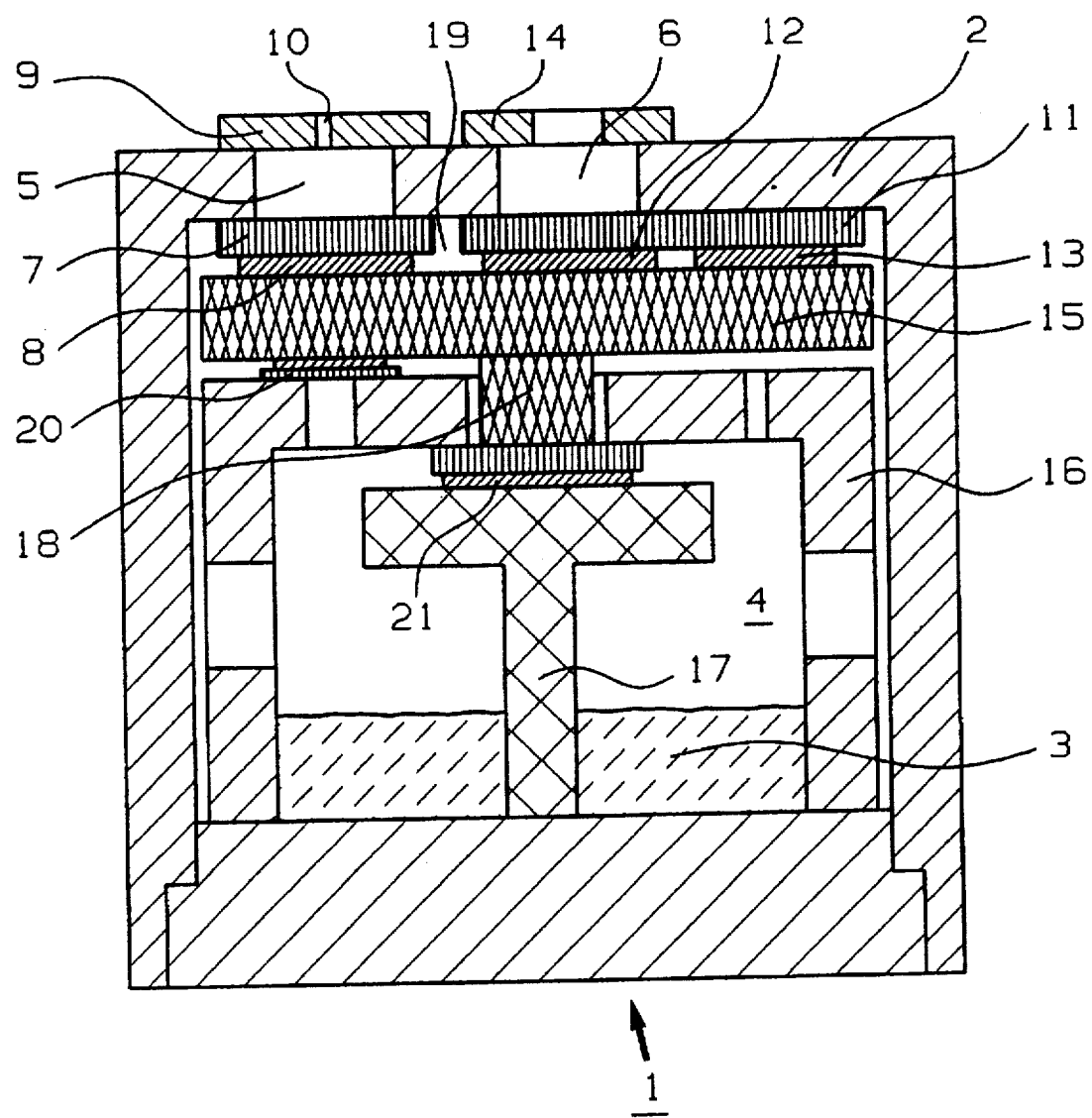

ELECTROCHEMICAL MEASURING CELL

BACKGROUND OF THE INVENTION

An arrangement for simultaneously detecting different gas components is disclosed in German patent publication 4,136,779. The arrangement includes a plurality of measuring electrodes, a common counter electrode and a common reference electrode in an aqueous electrolyte. The measuring electrodes are mounted behind a diffusion membrane and are subjected to the gas components to be detected via individual diaphragms forward of the diffusion membrane. These diaphragms limit the inflow of the gas. The formation of the measurement value takes place with the aid of a potentiostatic evaluating circuit which also controls the potentials on the measuring electrodes and also determines these potentials.

It is disadvantageous in this known arrangement that cross sensitivities occur because of diffusion of the gas components within the diffusion membrane. These cross sensitivities affect the selectivity of the detecting reaction. The cross sensitivity can be reduced by selecting specific work potentials. However, the sensitivity of the gas detection is affected during specific applications. On the other hand, there are detecting reactions wherein a lateral diffusion between two measuring electrodes is required, such as in the determination of carbon monoxide.

European patent publication 0,126,623 discloses an electrochemical measuring cell for detecting carbon monoxide. This measuring cell has two measuring electrodes and a gas path between the measuring electrodes. The known measuring cell has two platinum measuring electrodes as well as a platinum reference electrode and a platinum counter electrode. The measuring electrodes are mounted one behind the other and a partially hydrophobic and partially hydrophilic matrix lies between the measuring electrodes. The first measuring electrode is disposed on the upper end of the measuring cell and is subjected directly to the gas to be measured. The entire carbon monoxide portion is oxidized on this measuring electrode. Hydrogen is present in addition to carbon monoxide and is partially oxidized also on the first measuring electrode and then diffuses through the hydrophobic matrix to the second measuring electrode where it is completely converted.

It is disadvantageous with this known measuring cell that a detection of additional gases is not possible.

SUMMARY OF THE INVENTION

It is an object of the invention to provide a measuring cell of the kind described above which is improved in that the selectivity of the different gas components to be detected is improved.

The electrochemical measuring cell of the invention is for detecting different gas components of a gas sample and includes: a housing having at least two openings directed toward the gas sample and defining an electrolyte chamber; an aqueous electrolyte contained in the chamber; a plurality of measuring electrodes disposed in the aqueous electrolyte; diffusion membrane means covering the measuring electrodes; a reference electrode common to the measuring electrodes; a counter electrode common to the measuring electrodes; the reference electrode and the counter electrode being disposed in the electrolyte so as to be in spaced relationship to each other and to the measuring electrodes; first and second individual aperture means for limiting the flow of the gas sample to individual ones of the measuring electrodes; and, electrolyte barrier means for defining an electrolyte barrier between at least one of the measuring electrodes and the remaining ones of the measuring electrodes to prevent a lateral diffusion within the diffusion membrane means.

The advantage of the invention is primarily seen in that a lateral diffusion between individual measuring electrodes is effectively prevented by an electrolyte barrier within the diffusion membrane. The electrolyte barrier can be configured in such a manner that the diffusion membrane is interrupted between the measuring electrodes and is welded to a carrier at the separating location.

The diffusion membrane is advantageously configured as a first diffusion membrane and a second diffusion membrane. The electrolyte barrier is a gap between the first diffusion membrane and the second diffusion membrane which is filled with electrolyte.

In an advantageous manner and to detect a first gas component, a first electrode is provided with a first diaphragm and, to detect a second component, a second measuring electrode is provided with a second diaphragm which limits the inflow of gas to the second measuring electrode. A third measuring electrode is connected to the second measuring electrode via the diffusion membrane functioning as a gas path. The electrolyte barrier is disposed in the diffusion membrane between the first measuring electrode on the one hand, and the second and third measuring electrodes on the other hand.

Such a measuring cell is especially advantageously suited to detect a mixture of oxygen, carbon monoxide and hydrogen. The oxygen is reduced at the first measuring electrode. Carbon monoxide and a portion of the hydrogen are converted at the second measuring electrode. The portion of the hydrogen, which is not oxidized at the second measuring electrode, reaches the third measuring electrode via the diffusion path and is completely converted at this third measuring electrode. A lateral diffusion of oxygen from the second measuring electrode to the first measuring electrode is prevented by the electrolyte barrier in the diffusion membrane between the first measuring electrode on the one hand, and the second and third measuring electrodes on the other hand.

BRIEF DESCRIPTION OF THE DRAWING

The invention will now be described with reference to the single FIGURE of the drawing which shows a side elevation view, partially in section, of a measuring cell according to the invention.

DESCRIPTION OF THE PREFERRED EMBODIMENTS OF THE INVENTION

The measuring cell 1 includes a measuring cell housing 2 which encloses an electrolyte chamber 4 filled with an aqueous electrolyte 3. A first breakthrough 5 and a second breakthrough 6 are provided at the upper end of the measuring cell housing 2. The first breakthrough 5 is closed by a first diffusion membrane 7 and a first measuring electrode 8. The first measuring electrode 8 is applied to the first diffusion membrane 7 at the side thereof facing toward the electrolyte chamber 4. The entry of gas to the first diffusion membrane 7 is limited by a first diaphragm 9 having a capillary 10. The second breakthrough 6 is closed by a second diffusion membrane 11. In the region of the second breakthrough 6, a second measuring electrode 12 is mounted on the side facing toward the electrolyte chamber 4 and a third measuring electrode 13 is mounted outside of the overlap region of the second breakthrough 6.

The third measuring electrode 13 is connected via the second diffusion membrane 11 (functioning as a gas path) to the second breakthrough 6 and the second measuring electrode 12. The gas entry to the second diffusion membrane 11 is limited by a second diaphragm 14 disposed forward of the second breakthrough 6. A glass fiber mat 15, which is impregnated with the electrolyte 3, is pressed upon the measuring electrodes 8, 12 and 13. The glass fiber mat 15 communicates with the aqueous electrolyte 3 via a porous T-shaped member 17 and a porous intermediate piece 18.

A gap 19 is located between the first diffusion membrane 7 and the second diffusion membrane 11 and is filled with electrolyte 3. The gap 19 functions as an electrolyte barrier which prevents the diffusion of gas between the diffusion membranes 7 and 11. A reference electrode 20 and a counter electrode 21 are mounted within the electrolyte chamber 4 as common electrodes of the measuring electrodes 8, 12 and 13.

The measuring cell 1 of the invention is especially suitable for investigating a gas mixture comprising oxygen, carbon monoxide and hydrogen such as in the analysis of flue gas. The measuring electrodes (8, 12, 13), the reference electrode 20 and the counter electrode 21 are connected to a triple potentiostat (not shown) as known per se. The potential at the first measuring electrode 8 is so adjusted that all oxygen located in the breakthrough 5 is reduced at the first measuring electrode 8. The potentials of the second measuring electrode 12 and the third measuring electrode 13 are adjusted to approximately equal values in a manner that the carbon monoxide, which diffuses in via the second diaphragm 14 into the second breakthrough 6, is completely oxidized at the second measuring electrode 12 and that also the hydrogen is partially oxidized and that the excess hydrogen reaches the third measuring electrode 13 through the second diffusion membrane 11 and is completely converted at the third measuring electrode 13. A direct diffusion of oxygen from the region of the second measuring electrode 12 into the region of the first measuring electrode 8 is prevented by the electrolyte barrier 19 between the first diffusion membrane 7 and the second diffusion membrane 11.

It is understood that the foregoing description is that of the preferred embodiments of the invention and that various changes and modifications may be made thereto without departing from the spirit and scope of the invention as defined in the appended claims.

What is claimed is:

1. An electrochemical measuring cell for simultaneously detecting oxygen and carbon monoxide components of a gas sample, the electrochemical measuring cell comprising:

a housing having first and second openings directed toward the gas sample and defining an electrolyte chamber;

an aqueous electrolyte contained in said chamber;

a plurality of measuring electrodes disposed in said aqueous electrolyte;

a first diffusion membrane covering a first one of said measuring electrodes and a second diffusion membrane covering the remaining ones of said measuring electrodes;

a reference electrode common to said measuring electrodes;

a counter electrode common to said measuring electrodes;

said reference electrode and said counter electrode being disposed in said electrolyte so as to be in spaced relationship to each other and to said measuring electrodes;

first and second diaphragms corresponding to said first and second openings, respectively, for limiting the flow of said gas sample to individual ones of said measuring electrodes;

said first diaphragm being provided for a first one of said measuring electrodes for facilitating the detection of a first one of said components; said second diaphragm being provided for a second one of said measuring electrodes for facilitating the detection of said second one of said components;

a third one of said measuring electrodes being connected to said second measuring electrode via said second diffusion membrane with said second diffusion membrane defining a gas diffusion path between said second and said third measuring electrodes;

said first and second diffusion membranes being separate from each other and conjointly defining a gap therebetween; and said electrolyte filling said gap whereby said gap and said electrolyte in said gap conjointly defining a barrier to prevent transverse diffusion between said first measuring electrode and said remaining ones of said measuring electrodes.

2. The electrochemical measuring cell of claim 1, wherein said oxygen component is reduced at said first electrode and said carbon monoxide component is converted at said second measuring electrode.

3. The electrochemical measuring cell of claim 2, wherein hydrogen is present and a portion of said hydrogen is converted at said second measuring electrode and the remainder of said hydrogen diffuses through said second diffusion membrane to said third measuring electrode whereat said remainder of said hydrogen is converted.

* * * * *